US005417205A

United States Patent [19]

Wang

[11] Patent Number: 5,417,205

[45] Date of Patent: May 23, 1995

[54] AIR FILTER FOR THE NOSE

[76] Inventor: Jen-Yi Wang, No. 227, Sec. 1, Chung Shan Road, Yuanlin Town, Changhua County,

[21] Appl. No.: 255,244

[22] Filed: Jun. 7, 1994

[51] Int. Cl.[6] .............. A61M 15/08

[52] U.S. Cl. .............. 128/206.11; 128/204.12; 128/858

[58] Field of Search .............. 128/206.11, 205.29, 128/205.27, 204.12, 204.13, 858, 857, 863, 846

[56] References Cited

U.S. PATENT DOCUMENTS

| | | | |
|---|---|---|---|
| 1,317,013 | 9/1919 | Ford | 128/204.12 |
| 2,162,583 | 6/1939 | Kjellsson | 128/206.11 |
| 2,192,093 | 2/1940 | Moore | 128/206.11 |
| 2,237,954 | 4/1941 | Wilson | 128/204.12 |
| 2,433,565 | 12/1947 | Korman | 128/204.12 |
| 2,672,138 | 3/1954 | Carlock | 128/206.11 |
| 2,890,695 | 6/1959 | Safstrom | 128/206.11 |
| 3,457,917 | 7/1969 | Mercurio | 128/204.12 |
| 3,463,149 | 8/1969 | Albu | 128/204.12 |
| 3,905,335 | 9/1975 | Kapp | 128/206.11 |
| 4,052,983 | 10/1977 | Bovender | 128/204.12 |
| 4,221,217 | 9/1980 | Amezcua | 128/206.11 |
| 4,267,831 | 5/1981 | Aguilar | 128/206.11 |
| 4,887,597 | 12/1989 | Holland | 128/206.11 |
| 5,113,857 | 5/1992 | Dickerman et al. | 128/206.11 |

FOREIGN PATENT DOCUMENTS

| | | | |
|---|---|---|---|
| 1154070 | 4/1958 | France | 128/206.11 |

*Primary Examiner*—Robert A. Hafer
*Assistant Examiner*—Michael O'Neill
*Attorney, Agent, or Firm*—Merchant, Gould, Smith, Edell, Welter & Schmidt

[57] ABSTRACT

An air filter including two filter units linked by a connecting element for inserting into the nostrils of the nose to filtrate air passing through, each filter unit including a barrel, a first wire gauze filter fastened to the barrel at one end, a second wire gauze filter fastened to the barrel at an opposite end, and a stack of wet filter cloth received inside the barrel and retained between the first wire gauze filter and the second wire gauze filter.

6 Claims, 5 Drawing Sheets

AIR FILTER FOR THE NOSE

BACKGROUND OF THE INVENTION

The present invention relates to air filters, and relates more particularly to an air filter comprised of two filter units linked by a connecting element for fastening to the nostrils of the nose to filtrate air passing through.

While riding a motorcycle, working in a factory or repair workshop, people may wear a mask to filtrate inhaled air. A mask for this purpose is generally comprised of a small piece of cloth having two loops at two opposite sides for fastening to the ears. However, this structure of mask cannot effectively remove solid matter from inhaled air. When the mask is wet by rain water, it becomes sticky causing the user uncomfortable and difficult to speak or breathe. Because the mask is closely attached to the face, the skin of the face may be contaminated easily. As the mask is hung on the ears, the skin area of the ears may be hurt easily. When the mask is contaminated, it must be washed and sterilized before use. However, it is difficult to well wash the mask when it is inked by the user's lipstick. Furthermore, it is not polite to wear the mask while making a conversation with others.

SUMMARY OF THE INVENTION

The present invention has been accomplished under the circumstances in view. It is one object of the present invention to provide an air filter for the nose which can be fastened to the nose and concealed from the sight to filtrate solid matter from inhaled air. It is another object of the present invention to provide an air filter for the nose which is replaceable. It is still another object of the present invention to provide an air filter for the nose which is comfortable in use.

According to one aspect of the present invention, the air filter is comprised of two filter units linked by a connecting element for inserting into the nostrils of the nose to remove solid matter from inhaled air, wherein each filter unit comprises a barrel, a first wire gauze filter fastened to the barrel at one end, a second wire gauze filter fastened to the barrel at an opposite end, and a stack of wet filter cloth received inside the barrel and retained between the first wire gauze filter and the second wire gauze filter.

According to another aspect of the present invention, the barrel and the first and second wire gauze filters of each filter unit are respective made from silicon rubber, and therefore the filter units do not hurt the nose when they are respectively inserted into the nostrils.

According to another aspect of the present invention, the first wire gauze filter has a plurality of toothed triangular rod respectively perpendicularly extended from a filter body thereof for detachably holding the stack of wet filter cloth inside the barrel, and therefore the stack of wet filter cloth is replaceable.

DETAILED DESCRIPTION OF THE PREFERRED EMBODIMENT

Figure 1:
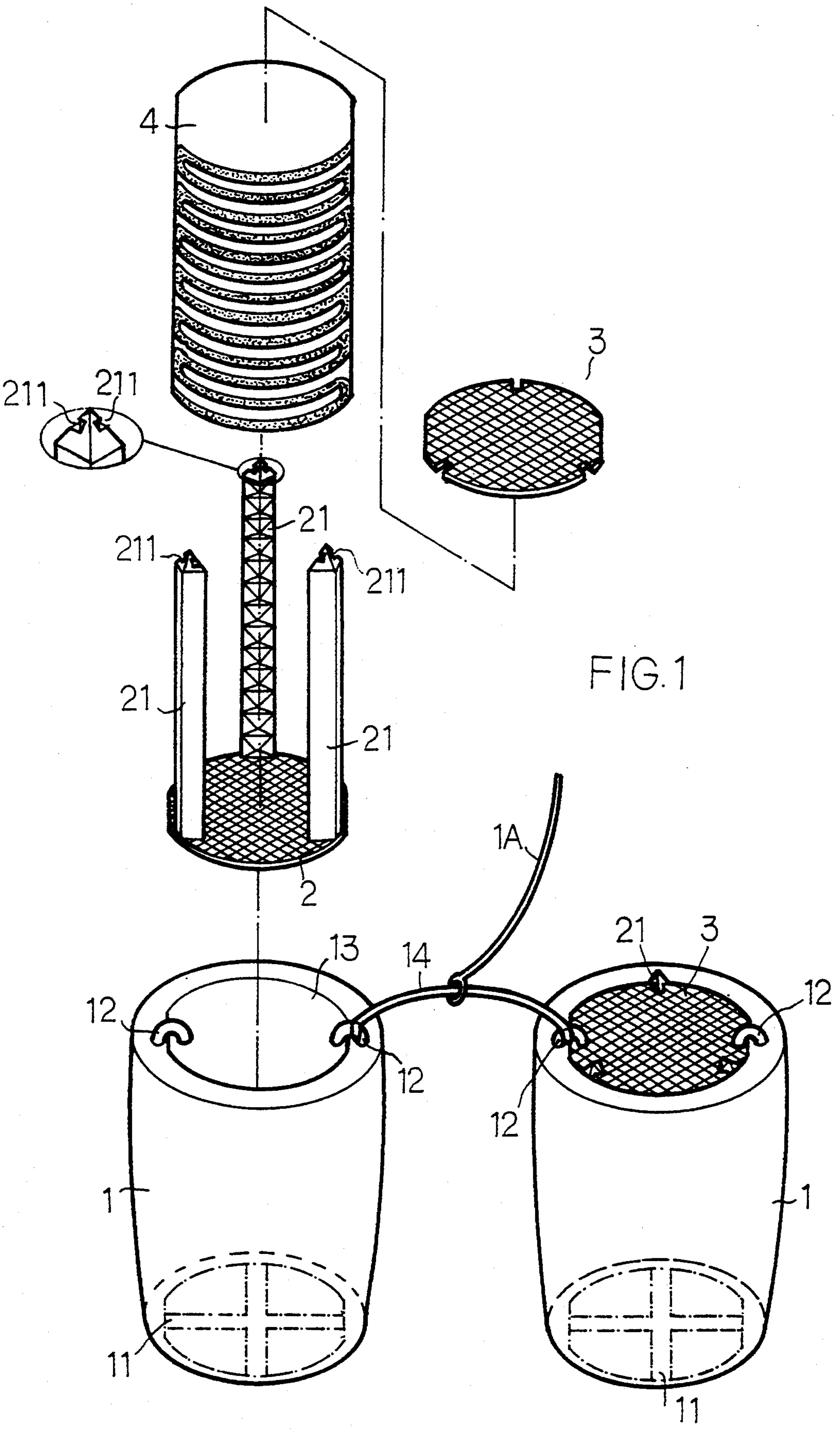
FIG. 1 is an exploded view of an air filter according to the present invention.
Figure 2:
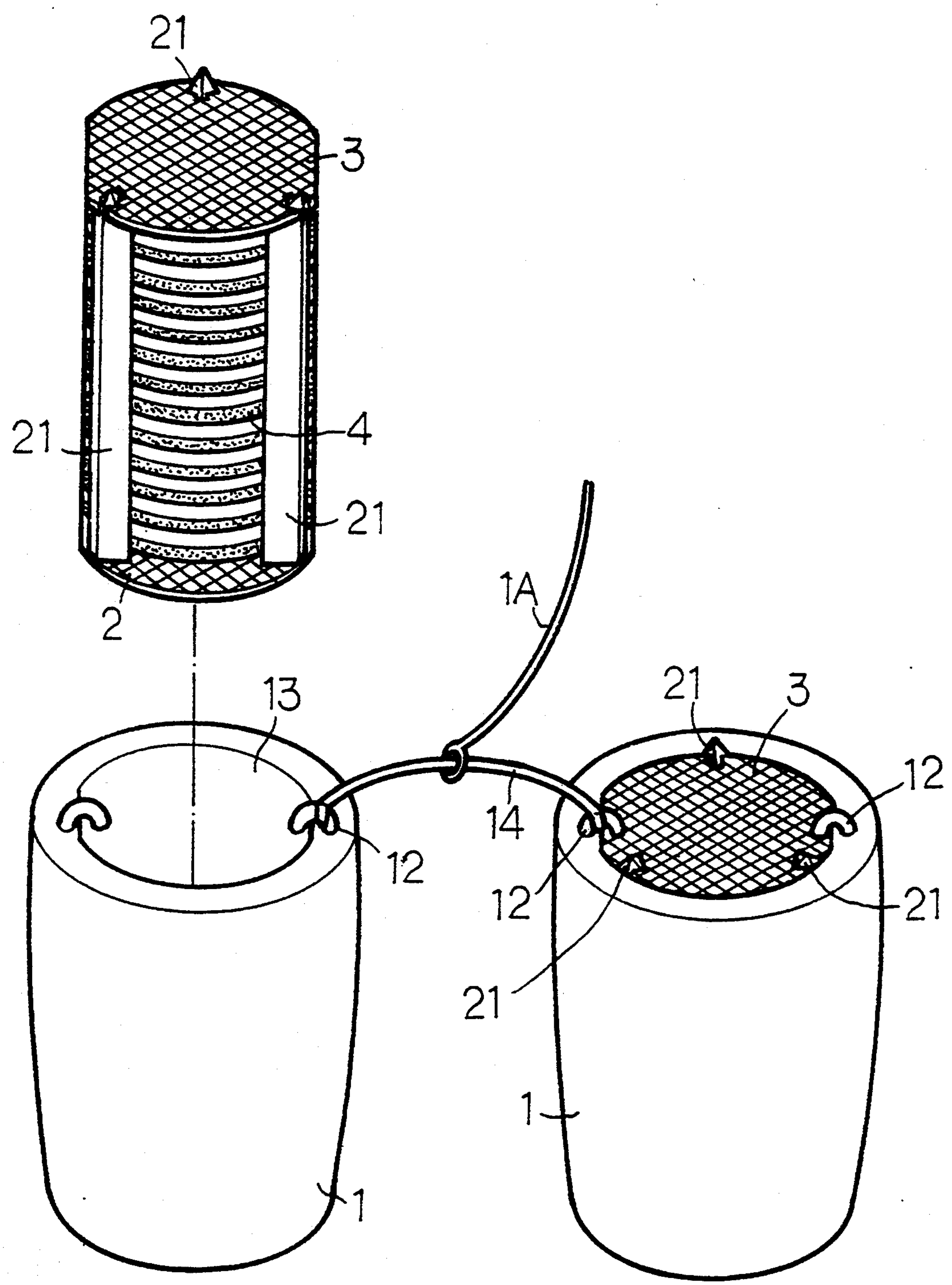
FIG. 2 is a perspective assembly view of the air filter shown in FIG. 1.
Figure 3:
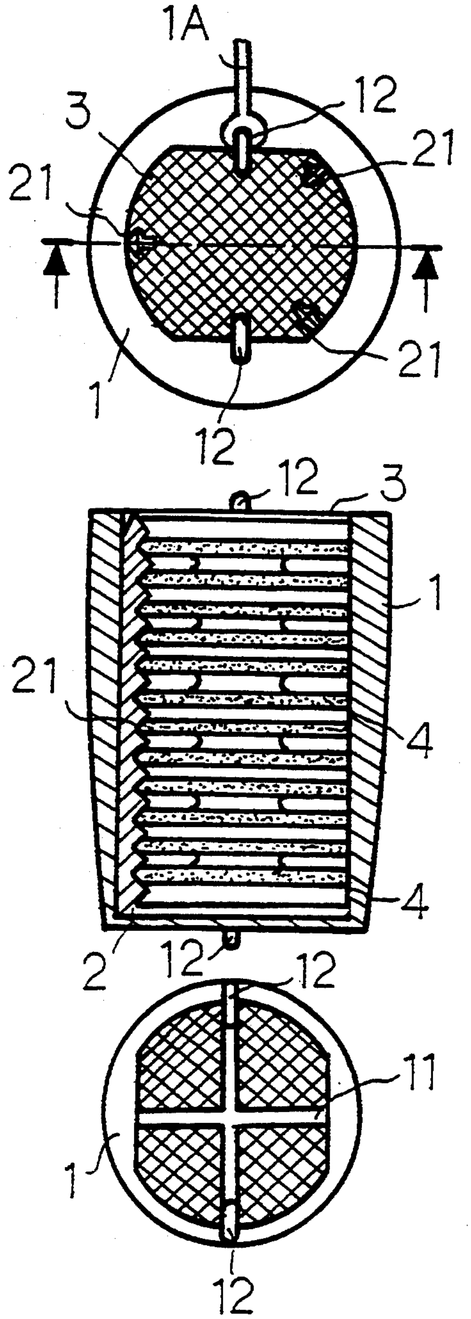
FIG. 3 is the front, top and bottom views of the air filter shown in FIG. 2.

Referring to FIGS. 1, 2, and 3, an air filter in accordance with the present invention is generally comprised of two barrels 1 joined by a connecting element 14 for inserting into the nostrils of the nose respectively. The barrel 1 is a hollow container defining an open chamber 13 for holding a first wire gauze filter 2 and a second wire gauze filter 3 and a stack of wet filter cloth 4, having a crossed rib 11 over the bottom end thereof and two curved springy stop rods 12 bilaterally disposed at the top end thereof. The first wire gauze filter 2 is mounted within the open chamber 13 of the barrel 1 and supported on the crossed rib 11 to hold the stack of wet filter cloth 4, having three toothed, triangular upright rods 21 equiangularly spaced from one another and disposed along the inside wall of the barrel 1 in the longitudinal direction. Each upright rod 21 of the first wire gauze filter 2 has a retainer portion 211 at the top. The second wire gauze filter 2 is fastened to the retainer portions 211 of the upright rods 21 of the first wire gauze filter 2 and covered over the stack of wet filter cloth 4 at the top and retained in flush with the top end of the barrel 1 by the springy stop rods 12. The barrel 1 and the first and second wire gauze filters 2 and 3 are respectively made from silicon rubber, therefore the barrel 1 can be inserted into either nostril of the nose comfortably. The aforesaid connecting element 14 has two opposite ends respectively fastened to either springy stop rod 12 of either barrel 1.

Figure 4:
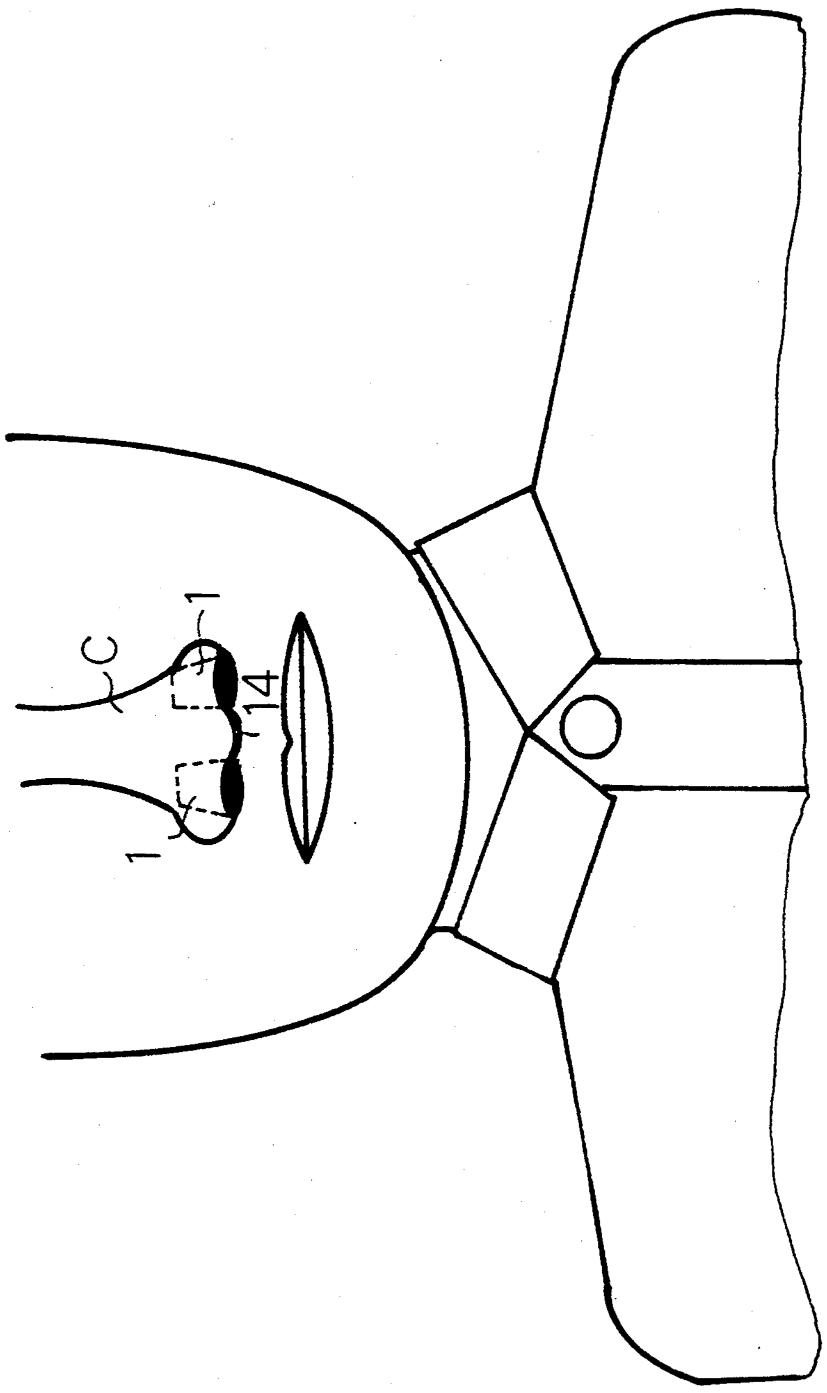
FIG. 4 is an applied view showing the air filter of the present invention fastened to the nostrils of the nose.

Referring to FIG. 4, the two barrels 1 of the air filter are respectively inserted into the nostrils of the nose C to filtrate air passing through. Because the stack of wet filter cloth 4 is retained inside the barrel 1, it does not dry out quickly. Therefore, the air filter can effectively remove solid matter from air passing through. The stack of wet filter cloth 4 can be replaced after a certain length of time in use or when it dries out.

Figure 5:
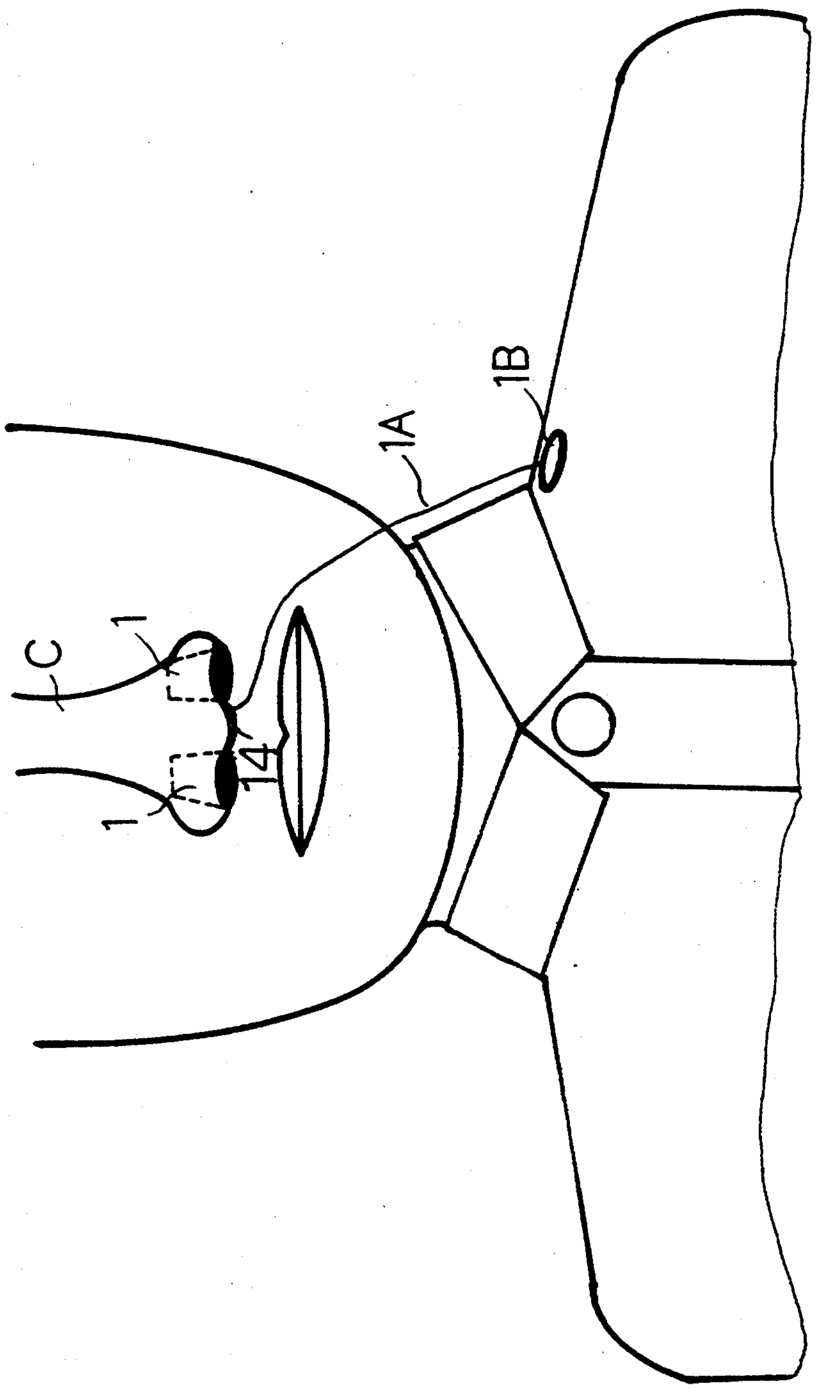
FIG. 5 is similar to FIG. 4 but showing a fastener connected to the connecting element of the air filter and fastened to the user's clothes.

Referring to FIG. 5, a fastener 1B may be provided and connected to the connecting element 14 for fastening the air filter to the user's clothes.

While only one embodiment of the present invention has been shown and described, it will be understood that various modifications and changes could be made without departing from the spirit and scope of the invention.

What is claimed is:

1. An air filter comprising two filter units linked by a connecting element for inserting into nostrils of a nose to filtrate air passing through, each filter unit comprising a barrel, a first wire gauze filter fastened to said barrel at a first end, a second wire gauze filter fastened to said barrel at a second end, and a stack of wet filter cloth received inside said barrel and retained between said first wire gauze filter and said second wire gauze filter, said first wire gauze filter including a plurality of rods which extend perpendicularly from an inside wall of the first wire gauze filter toward the second wire gauze filter and are longitudinally disposed along an inside wall of the barrel.

2. The air filter of claim 1 wherein the rods of said first wire gauze filter hold said stack of wet filter cloth inside said barrel, the rods have teeth formed along an outer wall of the rods, the second wire gauze filter is retained by the teeth so as to cover the stack of wet filter cloth inside the barrel at the second end.

3. The air filter of claim 1 wherein said first wire gauze filter is detachably fastened to said barrel so that said stack of wet filter cloth is replaceable.

4. The air filter of claim 2 wherein the barrel further includes a plurality of stop rods which are bilaterally disposed at the second end of the barrel, the stop rods further retain the second wire gauze filter in place to cover the stack of wet filter cloth.

5. The air filter of claim 4 wherein the connecting element has two opposite ends, each of which is fastened to one of the stop rods of each filter unit.

6. The air filter of claim 5 wherein the connecting element is connected to a releasing rope which is fastened to a user's clothes at an other end.

* * * * *